(12) United States Patent
Audureau et al.

(10) Patent No.: US 9,725,318 B2
(45) Date of Patent: Aug. 8, 2017

(54) METHOD FOR PREPARING IMIDE SALTS CONTAINING A FLUOROSULPHONYL GROUP

(71) Applicant: ARKEMA FRANCE, Colombes (FR)

(72) Inventors: Sophie Audureau, Feyzin (FR); Grégory Schmidt, Mornant (FR)

(73) Assignee: ARKEMA FRANCE, Colombes (FR)

( * ) Notice: Subject to any disclaimer, the term of this patent is extended or adjusted under 35 U.S.C. 154(b) by 25 days.

(21) Appl. No.: 14/370,696

(22) PCT Filed: Nov. 19, 2013

(86) PCT No.: PCT/FR2013/052785
§ 371 (c)(1),
(2) Date: Jul. 3, 2014

(87) PCT Pub. No.: WO2014/080120
PCT Pub. Date: May 30, 2014

(65) Prior Publication Data
US 2015/0246812 A1    Sep. 3, 2015

(30) Foreign Application Priority Data

Nov. 22, 2012  (FR) .................................... 12 61127

(51) Int. Cl.
| C01B 21/086 | (2006.01) |
| C01B 21/093 | (2006.01) |
| C07C 303/40 | (2006.01) |

(52) U.S. Cl.
CPC ........ *C01B 21/086* (2013.01); *C01B 21/0935* (2013.01); *C07C 303/40* (2013.01)

(58) Field of Classification Search
CPC .. C01B 21/086; C01B 21/0935; C07C 303/40
See application file for complete search history.

(56) References Cited

U.S. PATENT DOCUMENTS

| 2004/0097757 A1 | 5/2004 | Cernik et al. |
| 2009/0292105 A1 | 11/2009 | Michot |
| 2012/0232285 A1 | 9/2012 | Michot |

FOREIGN PATENT DOCUMENTS

| CN | 101 654 229 A | 2/2010 |
| CN | 102046523 A | 5/2011 |
| CN | 102617414 A | 8/2012 |
| EP | 2 674 395 A1 | 12/2013 |
| JP | 2004 522681 A | 7/2004 |
| RU | 2183621 | * 6/2002 |
| WO | WO 02/053494 A1 | 7/2002 |
| WO | WO 2007/068822 A2 | 6/2007 |
| WO | 2009/123328 A1 | 10/2009 |
| WO | 2012/108284 A1 | 8/2012 |
| WO | WO 2012/108384 A1 | 8/2012 |

OTHER PUBLICATIONS

English Translation of RU2183621, pp. 1-8, Jun. 2002.*
Ruff et al., "Imidodisulfuryl Fluoride, Cesium Imidodisulfuryl Fluoride, and Fluoroimidodisulfuryl Fluoride: [Imidobis (Sulfuryl Fluoride), Cesium Imidobis(Sulfulyl Fluoride), and Fluoroirnidobis-(Sulfuryl Fluoride)]", Inorganic Syntheses, Jan. 5, 2007, vol. 11, pp. 138-143.
Appel et al., "Die Synthese des Imidobisschwefelsäurefluorids, HN(SO2F)2", Chemische Berichte, Jan. 21, 2006, vol. 95, Issue 1, pp. 246-248. (And, English-language abstract).
International Search Report (PCT/ISA/210) mailed on Feb. 19, 2014, by the European Patent Office as the International Searching Authority for International Application No. PCT/FR2013/052785.
Office Action issued in Chinese Application No. 201380056760.8 on Mar. 18, 2016, with English language translation (9 pages).
An English Translation of the Japanese Office Action (Notice of Rejection) dated May 16, 2017, by the Japanese Patent Office in Japanese Patent Application No. 2015-543497. (2 pages).

* cited by examiner

Primary Examiner — Paul A Zucker
Assistant Examiner — Mark Luderer
(74) Attorney, Agent, or Firm — Buchanan Ingersoll & Rooney P.C.

(57) ABSTRACT

A fluorination process for obtaining fluorinated compounds including at least one fluorosulfonyl group. More particularly, a process for preparing a fluorinated compound of formula (II), including at least one step of reacting a compound of formula (I) with anhydrous hydrofluoric acid in at least one organic solvent, in which R1 is equal to R2 except in the specific case where R1=Cl, then R2=F, and when R1 is equal to R2, R1 and R2 represent an electron-withdrawing group which has a Hammett parameter σp of greater than 0, such as F, $CF_3$, $CHF_2$, $CH_2F$, $C_2HF_4$, $C_2H_2F_3$, $C_2H_3F_2$, $C_2F_5$, $C_3F_7$, $C_3H_2F_5$, $C_3H_4F_3$, $C_3HF_6$, $C_4F_9$, $C_4H_2F_7$, $C_4H_4F_5$, $C_5F_{11}$, $C_3F_5OCF_3$, $C_2F_4OCF_3$, $C_2H_2F_2OCF_3$, $CF_2OCF_3$, $C_6F_{13}$, $C_7F_{15}$, $C_8F_{17}$ or $C_9F_{19}$, and M represents a hydrogen atom, an alkali metal, an alkaline-earth metal or a quaternary ammonium cation.

18 Claims, No Drawings

METHOD FOR PREPARING IMIDE SALTS CONTAINING A FLUOROSULPHONYL GROUP

CROSS REFERENCE TO RELATED APPLICATIONS

The present application is a U.S. National Stage application of International Application No. PCT/FR2013/052785, filed on Nov. 19, 2013, which claims the benefit of French Application No. 1261127, filed on Nov. 22, 2012. The entire contents of each of International Application No. PCT/FR2013/052785 and French Application No. 1261127 are hereby incorporated herein by reference in their entirety.

TECHNICAL FIELD

The disclosure relates to a fluorination process for obtaining fluorinated compounds comprising at least one fluorosulfonyl group.

TECHNICAL BACKGROUND

Anions of sulfonyl imide type, by virtue of their very low basicity, are increasingly prevalent in the field of energy storage in the form of inorganic salts in batteries or organic salts in supercondensers or in the field of ionic liquids. Since the battery market is in full expansion and the reduction of battery manufacturing costs is becoming a major challenge, a process for large-scale and low-cost synthesis of anions of this type is necessary.

In the specific field of Li-ion batteries, the salt currently most commonly used is $LiPF_6$, but this salt shows numerous disadvantages, such as limited thermal stability, instability to hydrolysis and therefore lower safety of the battery. Recently, new salts having the $FSO_2^-$ group have been studied and have demonstrated numerous advantages, for instance better ionic conductivity and resistance to hydrolysis. One of these salts, LiFSI ($LiN(FSO_2)_2$), has shown very advantageous properties which make it a good candidate for replacing $LiPF_6$.

Few processes for the synthesis of LiFSI or of its corresponding acid have been described, but it is clearly apparent that, in all these processes, the key step is the S—F bond formation step.

The first synthesis route described (Appel & Eisenbauer, Chem Ber. 95, 246-8, 1962) consists in reacting fluorosulfonic acid ($FSO_3H$) with urea. The use of $FSO_3H$ thus makes it possible to already have the S—F bond formed, but the corrosive and toxic nature of this product did not allow industrialization of the process.

A second route (Ruff & Lustig, Inorg. Synth. 1968, 11, 138_43) consists in, firstly, synthesizing a dichlorinated compound having the following formula $(ClSO_2)_2NH$, and then performing chlorine/fluorine exchange with $AsF_3$. However, this process is not industrializable owing to the high price and the toxicity of $AsF_3$.

Document WO 02/053494 describes a third route which consists of a Cl/F exchange on $(ClSO_2)_2NH$ using a fluoride of a monovalent cation which may be an alkali metal cation or a cation of onium type ($NR_4^+$), in an aprotic solvent. According to said document, the reaction proves to be very slow.

Example 10 of document WO 07/068822 describes the synthesis of bis(fluorosulfonyl)imide in anhydrous hydrofluoric acid. Thus, the reaction is carried out in an autoclave with 1 g of bis(chlorosulfonyl)imide and 4 g of anhydrous HF at various reaction temperatures and times. Said document teaches that, even at temperatures of 130° C., the reaction yield does not exceed 55%. In addition, it teaches that the presence of impurities makes the separation difficult on an industrial scale. Said document concludes that the synthesis of bis(fluorosulfonyl)imide using HF is not satisfactory, and recommends the use of a lithium fluoride.

Despite this preconception, the applicant has developed a process for manufacturing fluorinated compounds comprising at least one fluorosulfonyl group (including bis(fluorosulfonyl)imide) by making use of anhydrous hydrofluoric acid. This process has the advantage of being easy to extrapolate to an industrial scale and HF also has the advantage of being inexpensive.

DETAILED DESCRIPTION

The applicant has observed, surprisingly, that when reacting a compound of formula (I)—$R_1(SO_2)_2ClNM$ with anhydrous hydrofluoric acid in an organic solvent, the yield in terms of fluorinated compound is virtually quantitative.

The process for preparing fluorinated compounds, according to the disclosure, comprises at least one step of reacting a compound of formula (I) with anhydrous hydrofluoric acid in at least one organic solvent. The step of reacting with anhydrous hydrofluoric acid, according to the disclosure, can be represented schematically as follows:

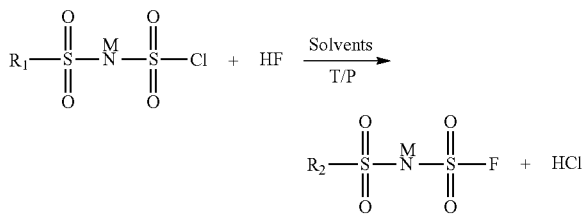

in which:
R$_1$ is equal to R$_2$ except in the specific case where R$_1$=Cl, then R$_2$=F. When R$_1$ is equal to R$_2$, R$_1$ and R$_2$ represent an electron-withdrawing group which has a Hammett parameter $\sigma_p$ of greater than 0, such as F, $CF_3$, $CHF_2$, $CH_2F$, $C_2HF_4$, $C_2H_2F_3$, $C_2H_3F_2$, $C_2F_5$, $C_3F_7$, $C_3H_2F_5$, $C_3H_4F_3$, $C_3HF_6$, $C_4F_9$, $C_4H_2F_7$, $C_4H_4F_5$, $C_5F_{11}$, $C_3F_5OCF_3$, $C_2F_4OCF_3$, $C_2H_2F_2OCF_3$, $CF_2OCF_3$, $C_6F_{13}$, $C_7F_{15}$, $C_8F_{17}$ or $C_9F_{19}$;

M represents a hydrogen atom, an alkali metal, an alkaline-earth metal or a quaternary ammonium cation.

The organic solvent preferably has a donor number of between 1 and 70, advantageously between 5 and 65. The donor number of a solvent represents the value –ΔH, ΔH being the enthalpy of interaction between the solvent and antimony pentachloride (Journal of Solution Chemistry, vol. 13, No. 9, 1984). As solvent, mention may in particular be made of esters, nitriles or dinitriles, ethers or diethers, amines or phosphines.

Methyl acetate, ethyl acetate, butyl acetate, acetonitrile, propionitrile, isobutyronitrile, glutaronitrile, dioxane, tetrahydrofuran, triethylamine, tripropylamine, diethylisopropylamine, pyridine, trimethylphosphine, triethylphosphine and diethylisopropylphosphine may be suitable as solvents.

The step of reacting with anhydrous hydrofluoric acid may be carried out at a temperature T preferably of between 0° C. and the boiling point of the solvent or of the mixture of solvents used. Advantageously, this temperature is between 5° C. and the boiling point of the solvent or of the mixture of solvents.

According to the disclosure, the step of reacting with anhydrous hydrofluoric acid may be carried out at a pressure P preferably of between 0 and 16 bar absolute.

The process according to the disclosure is preferably carried out by dissolving the compound of formula (I) in the solvent or the mixture of solvents prior to the step of reacting with anhydrous HF.

The weight ratio between the compound of formula (I) and the solvent or the mixture of solvents is preferably between 0.001 and 10 and advantageously between 0.005 and 5.

The HF is introduced into the reaction medium preferably in gaseous form.

The molar ratio between the compound of formula (I) and the HF used is preferably between 0.01 and 0.5 and advantageously between 0.05 and 0.5.

The step of reacting with HF can be carried out in a closed medium or in an open medium.

Without being bound by an explanation, the use of a donor solvent allows the formation of a solvent-HF complex and thus makes it possible to magnify the nucleophilicity of the fluorine atom. The use of such a complex allows mild fluorination of the compound of formula (I) while thus avoiding parasitic cleavage reactions.

The process according to the disclosure makes it possible to have fluorination yields of between 85% and 100%, which is a clear increase compared with the prior art processes.

When M in formula (I) is equal to H, the process according to the disclosure may comprise a cation exchange step after the fluorination step in order to obtain alkali metal salts, alkaline-earth metal salts or quaternary ammonium cation salts.

The process according to the disclosure is particularly advantageous for preparing fluorinated compounds having the following formulae: $LiN(FSO_2)_2$, $LiNSO_2CF_3SO_2F$, $LiNSO_2C_2F_5SO_2F$, $LiNSO_2CF_2OCF_3SO_2F$, $LiNSO_2C_3HF_6SO_2F$, $LiNSO_2C_4F_9SO_2F$, $LiNSO_2C_5F_{11}SO_2F$, $LiNSO_2C_6F_{13}SO_2F$, $LiNSO_2C_7F_{15}SO_2F$, $LiNSO_2C_8F_{17}SO_2F$ and $LiNSO_2C_9F_{19}SO_2F$.

Embodiments of the disclosure are illustrated by the following examples, to which it is not, however, limited.

EXAMPLE 1

In an 800 ml autoclave, 28 g of $(ClSO_2)_2NH$ are dissolved in 50 ml of acetonitrile. 10 g of HF are then added. The pressure is then 0.34 bar absolute and the temperature is maintained at 10° C. The reaction is left to stir in a closed medium for 18 h. The excess HF is removed by pumping. The reaction medium is then treated with lithium carbonate. The solution is filtered and then evaporated and the residue is analyzed by $^{19}F$ NMR. The analysis shows the presence of 85% of totally fluorinated product $(FSO_2)_2NLi$, 7.5% of $FSO_3Li$ and 7.5% of $FSO_2NH_2$. The latter two are the compounds formed during the degradation of the starting product.

EXAMPLE 2

In an 800 ml autoclave, 31.7 g of $(ClSO_2)_2NH$ are dissolved in 50 ml of acetonitrile. 10 g of HF are then added. The pressure is then 0.75 bar absolute and the temperature is maintained at 20° C. The reaction is left to stir in a closed medium for 18 h. The excess HF is removed by pumping. The reaction medium is then treated with lithium carbonate. The solution is filtered and then evaporated and the residue is analyzed by $^{19}F$ NMR. The analysis shows the presence of 100% of totally fluorinated product $(FSO_2)_2NLi$ and the absence of the degradation products $FSO_3Li$ and $FSO_2NH_2$.

EXAMPLE 3

In an 800 ml autoclave, 61 g of $(ClSO_2)_2NH$ are dissolved in 50 ml of 1,4-dioxane. 20 g of HF are then added. The pressure is then 2.3 bar absolute and the temperature is maintained at 25° C. The reaction is left to stir in a closed medium for 18 h. The excess HF is removed by pumping. The reaction medium is then treated with lithium carbonate. The solution is filtered and then evaporated and the residue is analyzed by $^{19}F$ NMR. The analysis shows the presence of 100% of totally fluorinated product $(FSO_2)_2NLi$ and the absence of the degradation products $FSO_3Li$ and $FSO_2NH_2$.

The invention claimed is:

1. A process for preparing a fluorinated compound of formula (II), comprising at least one step of reacting a compound of formula (I) with anhydrous hydrofluoric acid in at least one organic solvent according to the following scheme:

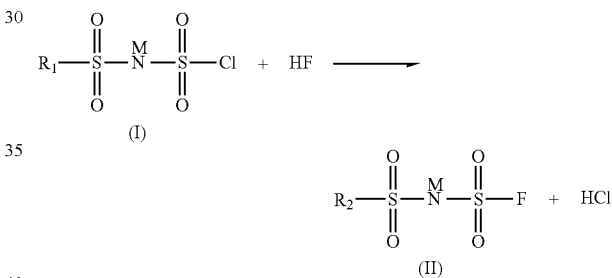

in which:
R$_1$ is equal to R$_2$ except in the specific case where R$_1$=Cl, then R$_2$=F, and
where R$_1$ is equal to R$_2$, R$_1$ and R$_2$ is an electron-withdrawing group which has a Hammett parameter $\sigma_p$ greater than 0 and is selected from the group consisting of F, $CF_3$, $CHF_2$, $CH_2F$, $C_2HF_4$, $C_2H_2F_3$, $C_2H_3F_2$, $C_2F_5$, $C_3F_7$, $C_3H_2F_5$, $C_3H_4F_3$, $C_3HF_6$, $C_4F_9$, $C_4H_2F_7$, $C_4H_4F_5$, $C_5F_{11}$, $C_3F_5OCF_3$, $C_2F_4OCF_3$, $C_2H_2F_2OCF_3$, $CF_2OCF_3$, $C_6F_{13}$, $C_7F_{15}$, $C_8F_{17}$ and $C_9F_{19}$, and
M is selected from the group consisting of a hydrogen atom, an alkali metal, an alkaline-earth metal and a quaternary ammonium cation.

2. The process as claimed in claim 1, wherein the at least one organic solvent has a donor number of between 1 and 70.

3. The process as claimed in claim 1, wherein the at least one organic solvent is selected from the group consisting of esters, nitriles or dinitriles, ethers or diethers, amines and phosphines.

4. The process as claimed in claim 1, wherein the reaction step is carried out at a temperature T of between 0° C. and the boiling point of the at least one organic solvent.

5. The process as claimed in claim 1, wherein the reaction step is carried out at a pressure P between 0 and 16 bar absolute.

6. The process as claimed in claim 1, wherein the compound of formula (I) is dissolved in the at least one organic solvent prior to the step of reacting with anhydrous HF.

7. The process as claimed in claim 1, wherein the weight ratio between the compound of formula (I) and the at least one organic solvent is between 0.001 and 10.

8. The process as claimed in claim 1, wherein the molar ratio between the compound of formula (I) and the HF used is between 0.01 and 0.5.

9. The process as claimed in claim 1, comprising a cation exchange step after the fluorination step in order to obtain alkali metal salts, alkaline-earth metal salts or quaternary ammonium cation salts.

10. The process as claimed in claim 1, wherein the compound of formula (II) is selected from the group consisting of $LiN(FSO_2)_2$, $LiNSO_2CF_3SO_2F$, $LiNSO_2C_2F_5SO_2F$, $LiNSO_2CF_2OCF_3SO_2F$, $LiNSO_2C_3HF_6SO_2F$, $LiNSO_2C_4F_9SO_2F$, $LiNSO_2C_5F_{11}SO_2F$, $LiNSO_2C_6F_{13}SO_2F$, $LiNSO_2C_7F_{15}SO_2F$, $LiNSO_2C_8F_{17}SO_2F$ and $LiNSO_2C_9F_{19}SO_2F$.

11. The process as claimed in claim 1, wherein the at least one organic solvent has a donor number of between 5 and 65.

12. The process as claimed in claim 1, wherein the reaction step is carried out at a temperature T of between 5° C. and the boiling point of the at least one organic solvent.

13. The process as claimed in claim 1, wherein the weight ratio between the compound of formula (I) and the at least one organic solvent is between 0.005 and 5.

14. The process as claimed in claim 1, wherein the molar ratio between the compound of formula (I) and the HF used is between 0.05 and 0.5.

15. The process as claimed in claim 1, wherein the process has a fluorination yield of between 85% and 100%.

16. The process as claimed in claim 1, wherein the at least one organic solvent is selected from the group consisting of methyl acetate, ethyl acetate, butyl acetate, acetonitrile, propionitrile, isobutyronitrile, glutaronitrile, dioxane, tetrahydrofuran, triethylamine, tripropylamine, diethylisopropylamine, pyridine, trimethylphosphine, triethylphosphine and diethylisopropylphosphine.

17. The process as claimed in claim 1, wherein the HF is in gaseous form.

18. The process as claimed in claim 1, wherein the compound of formula (II) is $LiN(FSO_2)_2$.

* * * * *